United States Patent [19]

Hausdorff

[11] 4,100,412
[45] Jul. 11, 1978

[54] SELECTIVE MULTICHANNEL OPTICAL TIME-SHARED DETECTOR FOR CHROMATOGRAPHY

[76] Inventor: Harry H. Hausdorff, 270 Westport Rd., Wilton, Conn. 06897

[21] Appl. No.: 737,106

[22] Filed: Oct. 29, 1976

[51] Int. Cl.² .............................. G01N 21/34
[52] U.S. Cl. .................... 250/343; 250/458
[58] Field of Search ........... 250/343, 458, 459, 461

[56] References Cited

U.S. PATENT DOCUMENTS

| 2,926,253 | 2/1960 | Munday | 250/343 |
| 3,832,548 | 8/1974 | Wallack | 250/343 |
| 3,869,613 | 3/1975 | Link et al. | 250/343 |
| 3,963,351 | 6/1976 | Chance et al. | 250/458 X |

Primary Examiner—Archie R. Borchelt
Attorney, Agent, or Firm—Frank J. Thompson

[57] ABSTRACT

An analytical apparatus is described having a non-dispersive, multiwavelength photometric analyzer which is adapted to provide simultaneous display of chromatography peaks at a plurality of different analytical wavelengths. In a particular arrangement, the apparatus includes a chromatograph for separating a sample to be examined into components.

13 Claims, 14 Drawing Figures

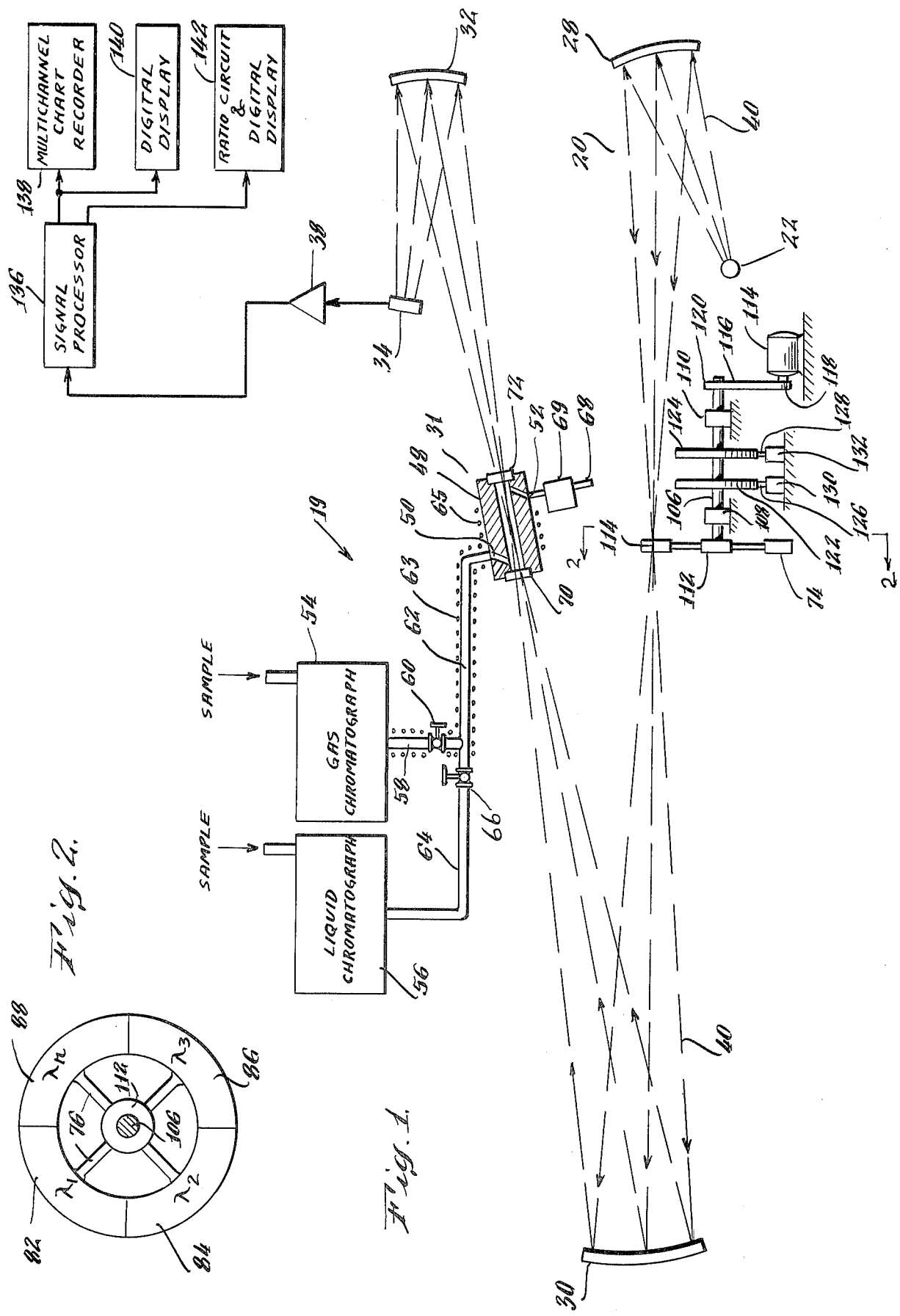

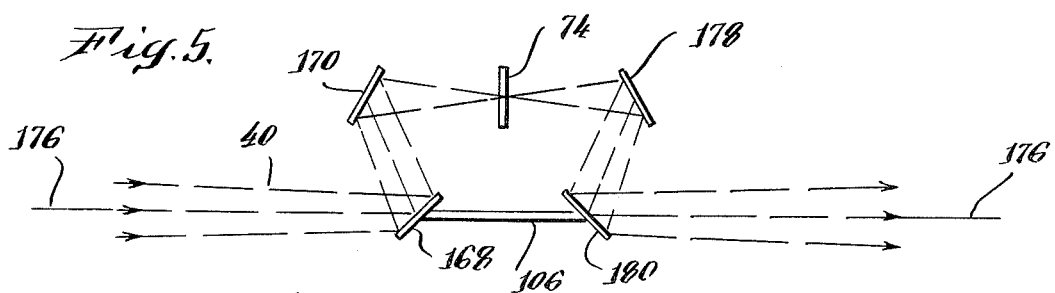
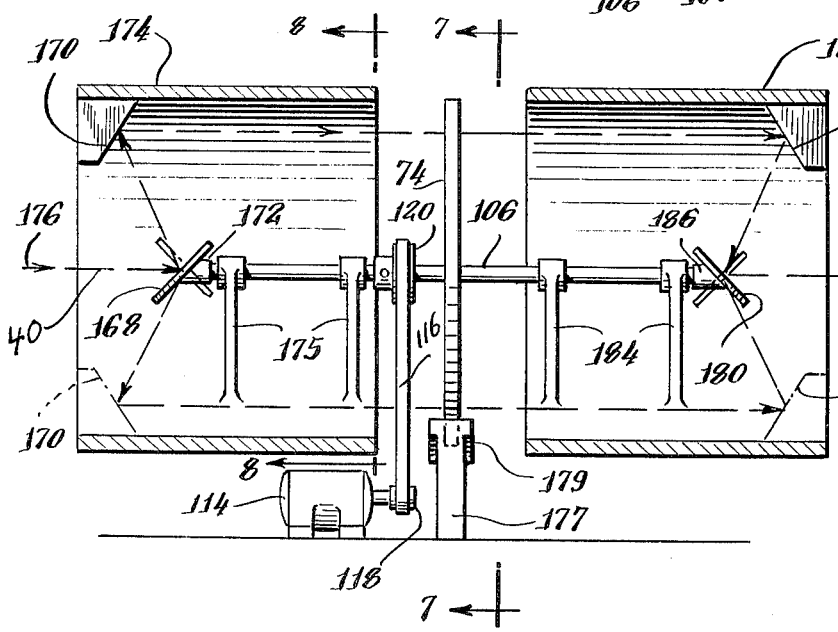
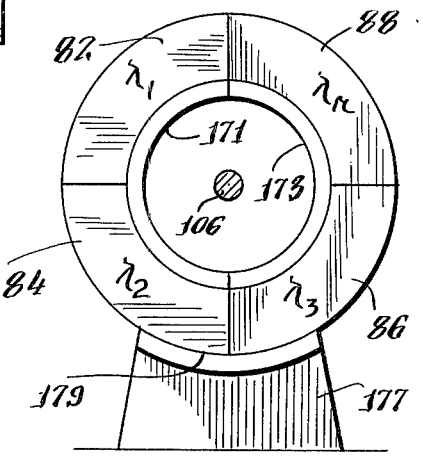
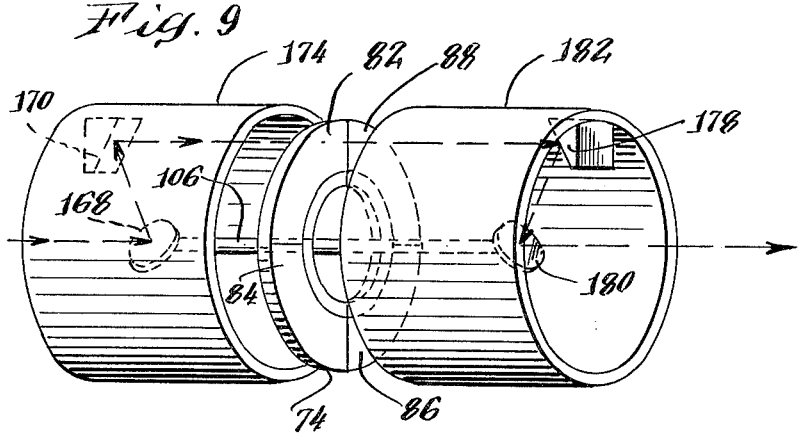
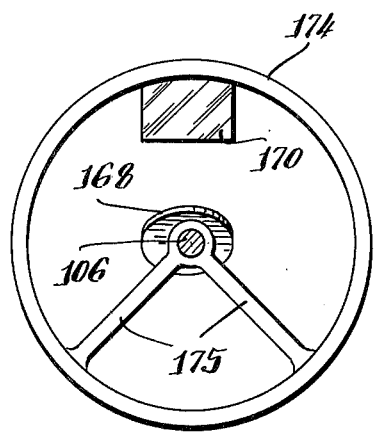
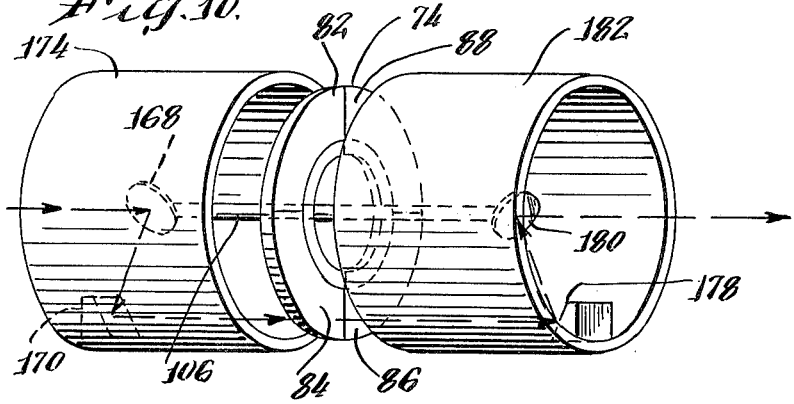

SELECTIVE MULTICHANNEL OPTICAL TIME-SHARED DETECTOR FOR CHROMATOGRAPHY

BACKGROUND OF THE INVENTION

This invention relates to an improved analytical instrument. The invention relates more particularly to an analytical instrument utilizing nondispersive photometric techniques.

Various analytical apparatus are known which are adapted for the examination of a sample substance and which provide a qualitative indication of sample components, a quantitative indication, or at times both qualitative and quantitative information. Present day apparatus of this type provide a sequential presentation in time of the information of interest for the analytical chemist. For example, the analysis of a sample with a chromatographic instrument will produce a chromatogram having a sequence of peaks, the heights or areas of which can be related to the quantities of sample constituents for a known sample volume. While certain substances have recognizable peak retention times which permit a trained observer to some extent to also identify substances, the chromatograph is generally considered to be a quantitative instrument which is relatively unsatisfactory for qualitative examination of a sample constituent. In a spectrophotometric type of analytical instrument, a sample under investigation is examined by scanning with radiant energy of different frequencies to determine the wavelengths of radiant energy absorption, emission, fluorescence, or reflectance by sample components. A spectrogram is generated indicating the wavelengths at which peaks corresponding to absorption, emission, fluorescence or reflectance occur. The spectrogram is utilized principally to provide peak information from which sample components or their structure can be identified. While the spectrophotometer is primarily a qualitative instrument, it may be used at times for quantitative determinations by a trained analytical chemist. In this regard it provides a relatively accurate determination of the ratio of components of a sample when not too many sample components are present at the same time.

Present day chromatographs and spectrophotometers include means for providing a visual display of a sample analysis through the use of various readout devices. The chart recorder is a readout device frequently used with chromatographs and spectrophotometers. In addition some instruments also include means for calculating and providing numerical readouts of peak areas, peak heights, etc. as for chromatograms obtained with chromatographs, and, spectrograms with spectrophotometers.

It is desirable to provide an analytical instrument having means for simultaneously displaying informational peaks of a substance being analyzed. Analysis would be further enhanced if the sample substance is initially separated into components by a chromatograph and each of the components is photometrically analyzed. For example, the simultaneous presentation of photometric peaks would be advantageous in examining the effluent components from a gas or liquid chromatograph or for monitoring the flow-through of a fluid material in a flow process. Photometric analysis at infrared (I.R.) frequencies is particularly useful since absorption frequencies exist which relate to functional groups in molecules and an observer can immediately determine from an absorption characteristic at a selected wavelength whether a component belongs to a particular class of molecules.

Analytical techniques are known wherein ultraviolet (U.V.) and fluorescence spectrophotometry and photometry at a preselected wavelength is utilized as a detection means with liquid chromatography. However, photometric techniques at the I.R. frequencies have not been utilized with liquid chromatography since most carrier liquids exhibit a relatively strong I.R. absorption characteristic which severely limits the analytical chemist in his selection of carrier liquids. While in the field of gas chromatography this carrier fluid limitation does not occur, nonetheless the relatively small sample volumes involved introduce a requirement for increased photometric sensitivity. A flow through detector cell for use with gas chromatography should have a volume of 20 microliters ($\mu$l) or less. In certain forms of gas chromatographic instruments such as those utilizing open tubular capillary columns, the volume should be even less. The use of I.R. photometry for qualitative detection of separated sample components is desirable in view of its capability for indicating molecular classes. However, the sensitivity and speed of an I.R. spectrophotometer is inadequate for examination of these relatively small separated samples. Special I.R. spectrophotometers which provide substantially higher sensitivities and speed are costly necessitating elaborate design, while the desired simultaneous display, referred to above, require relatively elaborate quantometers or rapid scanning photometers, each of which is also relatively costly.

Accordingly, it is an object of this invention to provide an improved form of analytical instrument.

Another object of the invention is to provide an analytical instrument having chromatographic separation means and nondispersive, multiwavelength photometric sample component identification means.

Another object of the invention is to provide an improved form of analytical instrument having a gas chromatographic separation means and a nondispersive, multiwavelength, I.R. photometric means of sample component identification.

Another object of the invention is to provide an analytical instrument of the type described of relatively reduced complexity and cost.

Another object of the invention is to provide a nondispersive photometer having multiwavlength means for simultaneously displaying radiant quantitative data at different wavelengths.

Another object of the invention is to provide a nondispersive, multiwavelength photometer of the type described of relatively reduced complexity and cost.

SUMMARY OF THE INVENTION

In accordance with features of the present invention, an analyzer is provided having a gas chromatographic separation means including a separation column which is adapted to separate an introduced sample into components which elute successively in time from the column. A detection means is provided and comprises a nondispersive, multiwavelength I.R. photometric analyzer. The analyzer includes an I.R. radiant energy source, a sample container means and a radiant energy filtering means which is positioned between the source and the container. The filtering means includes a reference filter member adapted to transmit radiant energy at a predetermined reference wavelength $\lambda_r$ and a plurality of analytical filter members each adapted to transmit radiant energy at different predetermined analytical wavelengths $\lambda_a$. Means are provided for projecting radiant energy in a beam from the source toward the sample container and from the container to a radiant energy detection means. Means are provided for causing the projected beam to periodically impinge upon each filter member whereby radiant energy at a plurality of differing wavelengths is periodically transmitted toward the sample container. The radiant energy detection means detects the intensity of radiant energy transmitted by the sample container and provides an electrical indication representative of the intensity. A means is coupled to the detection means for providing a simultaneous display of the intensity of radiant energy impinging on the detection means at each of the analytical wavelengths.

In accordance with other features of the invention, a non-dispersive, multiwavelength photometric analyzer comprises a radiant energy source, a radiant energy intensity detector means for providing an electrical indication representative of the intensity of radiant energy which impinges thereon, and a sample container means for positioning a sample under analysis in the path of a radiant energy beam whereby a sample positioned therein is impinged by incident radiant energy and absorbs radiation or fluoresces. First and second radiant energy projection means are provided for projecting radiant energy in a beam from the source toward the sample container means and from the sample container means toward the detector means respectively. A radiant energy filtering means is provided having a reference filter member and a plurality of analytical filter members each of which is adapted to transmit radiant energy at a different, predetermined wavelength. The filtering means is positioned in an optical path of a beam projected by the first or second projection means and a means is provided for causing the beam to periodically impinge upon and project through each of the filter members whereby radiant energy at a plurality of differing wavelengths is periodically transmitted by the filter means. In accordance with more particular features of the photometer of this invention, a means provides a simultaneous display of the intensity of radiant energy impinging on the detection means at each of the analytical wavelengths.

In accordance with more particular features of the invention, a means for causing the beam to periodically impinge upon and project through each of the filter members comprises a stationary assembly of filter members and means for deflecting the beam across the filter members. Detector selectivity is provided and is adapted to accommodate differing analytical situations through the substitution of filter assemblies. The provision of a stationary filter assembly renders the substitution of filters relatively simple and convenient for an operator and eliminates a need for careful alignment within the instrument.

An improved signal processing circuit means is also provided in accordance with features of the invention which converts a single channel sequential analog detector signal into multichannel parallel analog signals. The circuit means also provides a ratio between signals of differing output channels in the instrument thereby supplying further qualitative information for the user.

In accordance with still another feature of the invention, an optical arrangement of the instrument provides for a relatively narrow radiant energy beam and for projection of the beam through relatively low capacity sample cells. Cells for chromatographic uses have, for example, a volume of less than about 20 $\mu$1. This feature is particularly advantageous in chromatographic instruments since small amounts of separated components follow closely and rapidly through the cell. It eliminates the need for relatively expensive optical condensing systems which would not reduce sufficiently energy losses through vignetting because of their relatively large apertures.

The improved nondispersive, multiwavlength photometer of the invention is disclosed herein for use as a selective detector for gas and liquid chromatographs. It is equally useful in other areas including, but not limited to, process control, laboratory analysis, and pollution analysis. The nondispersing multiwavelength photometer is described hereinafter as being operated in the infrared and UV range and in the absorption and fluorescence modes. It is also operable, in accordance with the invention, in the visible range and in emission, reflectance and polarization modes.

BRIEF DESCRIPTION OF THE DRAWINGS

These and other objects and features of the invention will become apparent with reference to the following specification and to the drawings wherein:

FIG. 1 is a schematic diagram of a chromatograph having a nondispersive multiwavelength I.R. photometric detector means which is constructed in accordance with features of one embodiment of the present invention;

FIG. 2 is a view of a filter taken along line 2—2 of FIG. 1;

FIG. 5 is an optical schematic diagram of an alternative beam deflection means of FIG. 1;

FIG. 6 is an enlarged, side elevational view, partly in section, of the beam deflection arrangement of FIG. 5;

FIG. 7 is a view taken along lines 7—7 of FIG. 6;

FIG. 8 is a view taken along lines 8—8 of FIG. 6;

FIG. 9 is a perspective view of a portion of the beam deflection means of FIG. 6 illustrating projection of the beam for one rotational position of a reflector drive shaft;

FIG. 10 is a perspective view of a portion of the beam deflection means of FIG. 6 illustrating projection of the beam for another rotational position of the reflector drive shaft;

DETAILED DESCRIPTION

Figure 3:
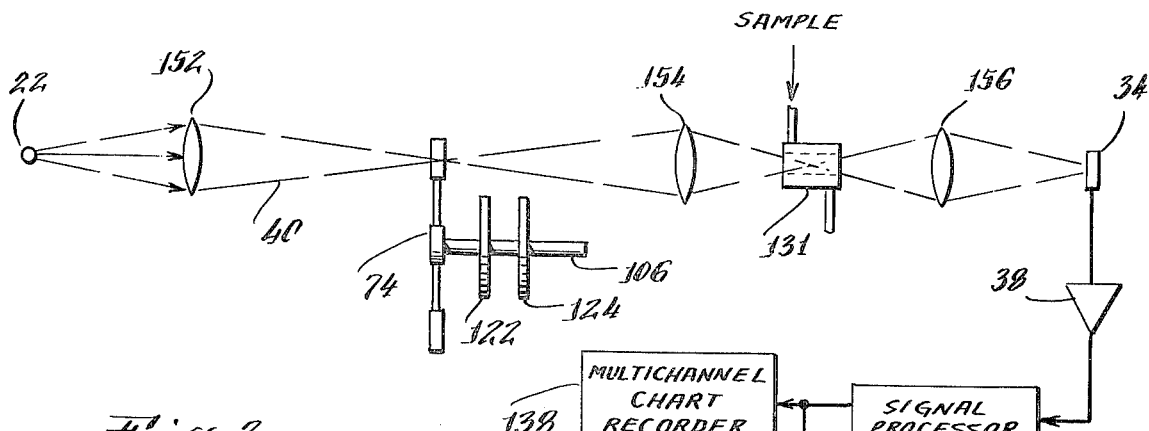
FIG. 3 is a schematic diagram of a nondispersive, multiwavelength photometer for operation in the U.V. range and constructed in accordance with features of this invention.

Referring now to FIG. 1, an analytical instrument is shown to comprise a chromatographic separation means indicated by reference numeral 19 and a detection means. The detection means comprises a nondispersive, multichannel photometer which is indicated generally by reference number 20. The photometer includes a suitable radiant energy source 22 for a desired spectral region. Various suitable sources are known. In FIG. 1, the photometer 20 is adapted for operation in the I.R. range and one such suitable comprises a heated nichrome wire. In the U.V range, the source may comprise a deuterium lamp while in the visible range it can comprise a tungsten lamp. Optical projection means are provided comprising reflective surfaces 28 and 30 for projecting radiant energy at a sample container means 31, and, reflective surface 32 for projecting radiant energy from the container means 31 to a radiant energy detector means 34. The detector means 34 is selected for the spectral range of operation. For the I.R. range, it may comprise a thermocouple detector. Radiant energy impinging on the detector means 34 results in the generation of an electrical signal which is applied to a preamplifier 38. This optical projection means projects radiant energy in a beam which is illustrated in FIG. 1 generally by the projection lines 40 and, while enlarged for emphasis in the drawing, it will be understood that the projecting means is adapted for projecting a relatively narrow beam. The optics have a relatively large F number which provides a relatively narrow beam. Sample container means 31 is a radiant energy transmissive, sample flow through cell which includes a heatable tubular shaped housing 48 having a sample inlet aperture 50 and an effluent outlet aperture 52. A sample to be analyzed is supplied to the sample container means 31 from a gas chromatograph 54 through heated capillary tubulation 58, a valve 60 and a heated manifold 62 or, alternatively, from a liquid chromatograph 56 through tubulation 64, a valve 66 and the manifold 62. The sample is initially introduced into the gas chromatograph 54 and is transported through a separating column, not illustrated, in the chromatograph in a well known manner by a carrier gas. During its transit through the separating column, the constituents of the sample are separated in time and are sequentially carried from the chromatograph by the carrier gas via the tubulation 58 and manifold 62 to the sample container means 31, through the sample container housing 48 and ultimately are discharged from the outlet aperture 52 into a flow meter 69 and an exhaust tubulation 68. A sample which is separated by the liquid chromatograph 56 is similarly carried by a liquid carrier through the tubulation 64 and the manifold 62 to the sample container means 46 and therefrom via the outlet apertures 52 and the exhaust tube 68.

The sample container means 31 further includes a gas tight inlet window 70 through which the beam 40 is transmitted and a gas tight outlet window 72 through which the beam 40 is transmitted from the sample container means. For any particular interval of time, a sample component in the container is impinged by radiant energy which projects into the sample container through the inlet window 70 and absorbs radiation. In view of the closely following eluted components occurring with gas or liquid chromatography, it is desirable that the sample volume of the container means 31 be relatively small. Instrument photometric sensitivity is directly proportional to absorption which in turn is proportional to the path length of sample material in the container or cells. Accordingly, it is preferable that the cell have a relatively small cross sectional area and a relatively long path within which radiant energy absorption occurs. The high F number optics referred to advantageously provides a relatively small beam dimension for use with sample cells having relatively small cross sections. In an exemplary arrangement wherein an open tubular column is employed, a typical sample volume is on the order of 20 $\mu l$ or less, and a cell is utilized having a volume of 7 $\mu l$, a diameter of 1 mm. and a path length of 1 cm. A variation in the intensity of the light beam 40 projected from the outlet window 72 occurs and this variation is sensed by detector 34 which provides a corresponding variation in the amplitude of an electrical signal.

A radiant energy filtering means, referenced generally as 74, is provided and is optically positioned in the path of the light beam 40 between the radiant energy source 22 and the sample container means 31. The radiant energy filtering means 74 includes a plurality of measuring filtering elements each adapted to transmit radiant energy at a predetermined analytical wavelengths $\lambda_a$ and a reference filter element adapted to transmit radiant energy at a predetermined wavelength $\lambda_r$. As illustrated in FIGS. 1 and 2 the radiant energy filtering means comprises a disk shaped assembly of filter members having the desired differing wavelength characteristics. The disk shaped assembly comprises a frame 76 which supports a plurality of filter members 82, 84, 86 and 88. The filter members 82, 84 and 86 comprise arcuate segments having a radiant energy transmissive characteristic at the wavelengths $\lambda_1$, $\lambda_2$ and $\lambda_3$ while the filter member 88 also comprises an arcuate segment which has a radiant energy transmissive characteristic for transmitting radiant energy at a wavelength $\lambda_r$. The wavelengths $\lambda_1$, $\lambda_2$, $\lambda_3$ are the analytical wavelengths $\lambda_a$ while the wavelength $\lambda_r$ comprises a reference wavelength where no sample absorption is likely to occur.

A means for causing the beam 40 to periodically impinge upon and project through each of the filter members is provided. This means provides for rotational movement of the filter means in the path of the beam 40 whereby radiant energy is periodically projected at a plurality of differing wavelengths toward the container means 31. The filter rotational means includes a drive shaft 106 which is rotatably supported in bearings 108 and 110. The shaft 106 is mounted to a hub 112 of the filter frame 76 and this assembly of filter means and shaft is positioned for providing that a cross section of the filter members is positioned at a focal point 114 of the reflective surfaces 28 and 30. The shaft is rotatably driven by an electric motor 114 through a belt 116 and pulleys 118 and 120. Disks 122 and 124, are also mounted on the shaft for rotation therewith. As described in detail hereinafter, these disks have cam segments 126 and 128 for periodically actuating pulse generators 130 and 132 respectively.

The projection of a light beam having distinct alternating wavelengths, rather than the continuous separation of the beam into wavelengths such as is accomplished with a scanning prism or grating monochromator is for the purposes of this specification and appended claims termed nondispersive and provides a nondispersive photometric examination of a sample constituent within the sample container means 31 of FIG. 1. A sample constituent will absorb or fluoresce at a particular wavelength depending upon the constituents thereof. By providing a simultaneous display of this photometric analysis, an analytical chemist will advantageously have available information for comparing the wavelength characteristics of a sample component at each of the wavelengths in making a determination as to the identity of the component. A means is coupled to the radiant energy detection means 34 for providing a simultaneous indication of the intensity of radiant energy impinging on the detection means at each of the plurality of wavelengths $\lambda_1$, $\lambda_2$, and $\lambda_3$. This means comprises a signal processing circuit means 136 for converting premplified serial analog signals from the detection means 34 into multichannel, parallel, analog signals. Each channel is associated with a wavelength $\lambda_1$, $\lambda_2$ or $\lambda_3$. The signal processing circuit means which is described in detail hereinafter also provides for converting each channel signal into an absorbance signal. The absorbance signals which are proportional to concentration are applied to a multichannel display means shown to be a chart recorder 138 coupled to the circuit means 136 for simultaneously displaying chromatograms for each signal component at each of the wavelengths $\lambda_1$, $\lambda_2$, and $\lambda_3$. The absorbance signals are simultaneously or alternatively coupled to a multichannel digital readout 140. For additional information, it is advantageous to provide an indication of the ratio of signal peaks or areas between signals of the different channels. The absorbance signals are coupled to a ratio circuit and digital display means 142 which provides and prints out desired ratios.

Figure 4:
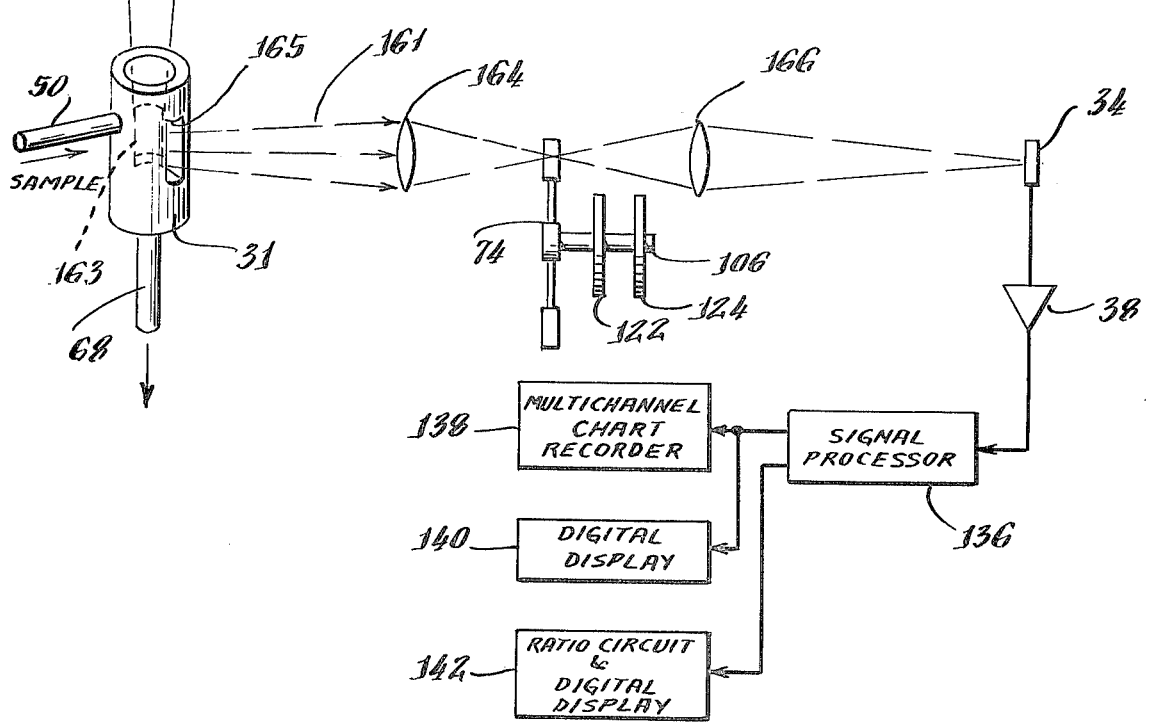
FIG. 4 is a schematic diagram of a nondispersive, multiwavelength fluorescence photometer constructed in accordance with features of this invention.

FIGS. 3 and 4 illustrate alternative arrangements of a nondispersive, multichannel photometer for operation in the U.V. spectral range and for operation in a fluorescing mode, respectively. Those elements of FIGS. 3 and 4 and of other figures described hereinafter which perform the same functions as elements described hereinbefore with respect to FIG. 1 bear the same reference numerals. The photometer of FIG. 3 includes optical projection means adapted for operation in the U.V. spectral range. This means comprise lenses 152 and 154 for projecting the light beam 40 from the source 22 toward the sample container means 31. A lens 156 is provided for projecting the beam from the container means 31 toward the detector 34. The sample container means, described hereinbefore, comprises a fixed sample cell or alternatively when used with a chromatograph, comprises a flow through cell.

In the fluorescence mode of operation as illustrated in FIG. 4, radiant energy from a source 158 is projected as an exciting beam 159 through an exciting wavelength filter 160 and a lens 162 toward an inlet window 163 of the sample container means 31.

For purposes of clarity in FIG. 4 of the drawing, the container means 31 is shown in perspective. Window 163 comprises a gas tight, radiant energy permeable slot extending in the direction of a longitudinal axis of the cylindrically shaped container. Incident radiant energy of exciting beam 159 impinges the container in a generally radial direction. Sample material in the container means is excited by this radiation and a fluorescent radiation in the form of a beam 161 is projected from the excited sample at an outlet window 165, at right angles, toward the radiant energy detector means 34 by lenses 164 and 166. In this arrangement, the filter means is positioned in the optical path at a location between the sample container means 31 and the detector means 34.

An alternative arrangement of a means for causing the beam 40 to periodically imping upon and project through each of the filter members is illustrated in FIGS. 5–10. This alternative arrangement is particularly advantageous in the I.R. range and for ease of filter substitution. In this arrangement the filter means 74 is stationary and a means is provided for deflecting the beam 40 and causing it to traverse a circular path about the disk assembly and to sequentially and repeatedly impinge upon the filter members 82, 84, 86 and 88. Deflection of the beam 40 and circular motion of the beam is provided by a first reflective means comprising first and second reflective impinge upon 168 and 170 respectively. The reflective surface 168 comprises a mirror which is supported on a hub 172 and is mounted to the shaft 106. Rotary motion is imparted to the shaft 106 from the electric motor 114 via the belt drive 116 and pulleys 118 and 120.

Reflective surface 170 comprises a mirror which is mounted to an inner surface of a cylinder 174. Cylinder 174 is supported by brackets 175 from the shaft 106 for rotation with the shaft. Beam 40 projects into cylinder 174 and impinges upon the mirror 168. The beam is thus reflected off an incident axis 176 and the mirror 168 is positioned and orientated for causing the reflected beam 40 to impinge upon the mirror 170. The mirrors 168 and 170 rotate upon rotation of the shaft 106 and the mirror 168 thus causes the beam 40 to be reflected off its axis 176 and to traverse a circular path as the shaft 106 rotates. The mirror 170 in turn is positioned and orientated for causing the beam 40 to be reflected in a direction generally normal to the filter means 74. The beam 40 thereby traverses a circular path along the disk assembly and is sequentially and periodically projected through the filter members 82, 84, 86 and 88. However, the radiation from source 22 which is transmitted through each of the filter members will be limited to the wavelength characteristic of the particular filter member. Thus, a light beam having a plurality of differing wavelengths occurring in sequence is provided. The light beam at these wavelengths is returned to and projected along the axis 176 toward the sample container means 31 (FIG. 1) by a reflective surface means comprising mirrors 178 and 180. The mirror 178 is supported from an inner surface of a cylinder 182 which is supported from shaft 106 by brackets 184 for rotation therewith. Mirror 178 is aligned with mirror 170 and the light beam 40 which is transmitted through the filters 82, 84, 86 and 88 impinges upon this mirror. The mirror 178 is positioned and orientated with respect to the mirror 180 for causing reflection of the light beam 40 incident thereon toward the mirror 180. The mirror 180 is supported on a hub 186 which is rotated with the shaft 106. Light incident upon the mirror 180 is reflected along the axis 176 and is transmitted through the cylinder 182 toward the sample container means 31 (FIG. 1). FIGS. 9 and 10 illustrate the projection of the light beam for different rotational positions of the shaft 106.

In FIG. 7, the radiant energy filtering members is shown to comprise a disk shaped assembly of filter members. The disk shaped assembly includes a first semicircular shaped frame support member 171 and a second semicircular shaped frame support member 173. The frame support members 171 and 173 each support a plurality of filter members 82, 84 and 86, 88 respectively. The semicircular frame support member 171 with its supported filter elements 82, 84 and the semicircular frame support member 173 with its supported filter elements 86, 88 are nested in a notch 179 of a support base 177. The members 171 and 173 are thereby supported about the shaft 106 and can be individually mounted and removed therefrom.

Figure 11:
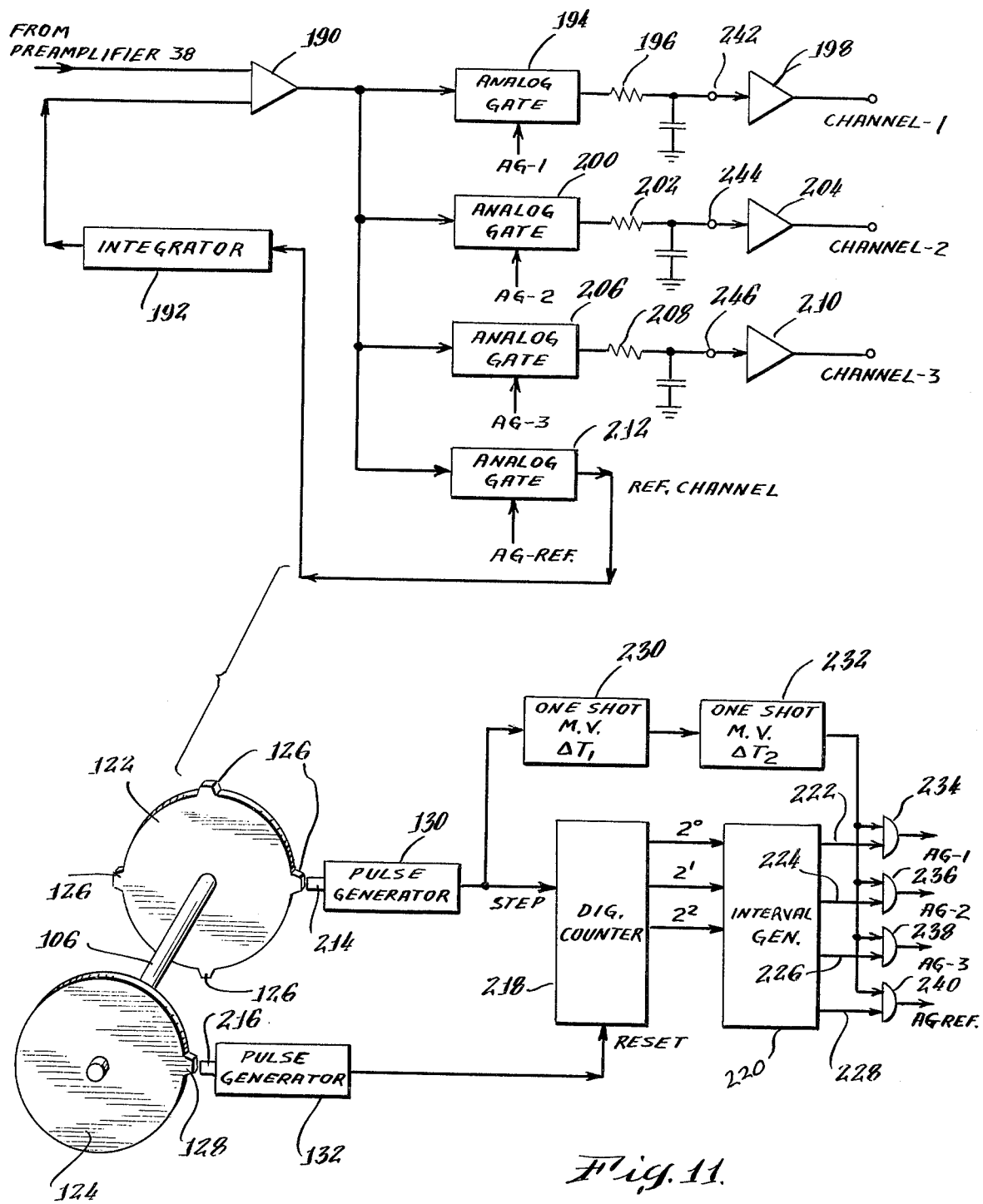
FIG. 11 is a circuit diagram, partly in schematic and partly in block form illustrating a circuit arrangement for use with the analyzer of FIG. 1 and constructed in accordance with one embodiment of the present invention.

The signal processing circuit means 136 of FIG. 1 is illustrated in greater detail in FIG. 11 and is shown to comprise a summing amplifier 190, an integrator 192 and a multichannel gating and amplifying arrangement. The latter circuit arrangement includes a first channel having an analog gate 194, a low pass RC filter 196 and buffer log amplifier 198; a second channel having an analog gate amplifier 200, a low pass RC filter 202 and a buffer and log amplifier 204; and, a third channel having an analog gate amplifier 206, a low pass RC filter 208 and a buffer amplifier 210. Additional channels can be provided as desired. An analog gate 212 is provided for a reference signal channel.

A gating signal generating means is provided and comprises the disk assemblies 122 and 124 which, as indicated hereinbefore, are positioned on and rotated by the shaft 106. Three disks include peripherally located actuating tabs 126 and 128, respectively. The disk 122 includes four equally spaced tabs 126 while the disk 124 has one tab 128. Rotation of the shaft causes the tabs to periodically engage associated actuating switch cams 214 and 216 of pulse generators 130 and 132 respectively. The generators 130 and 132 comprise, for example, multivibrators which are triggered by actuation of the switch cams 130 and 132 upon engagement by the tabs 126 and 128 respectively. The generator 130 will therefore generate four pulses for each rotation of the shaft 106 while the generator 132 will generate one pulse for each rotation of the shaft. The disks 122 and 124 and the tabs 126 and 128 respectively are indexed with respect to the filter disk means 74 for providing that the generator 130 provides an output pulse at the nominal time of transition of beam 40 between the filter members such as the members 82 and 84 of FIG. 2 while the pulse generator 132 generates an output pulse at the nominal time of beam transition between adjacent reference and analytical filter members such as the beam transition between the filter members 88 and 82 in FIG. 2. A digital counter 218 is provided and the counter is stepped by output pulses from the generator 130 and is reset by an output pulse from the generator 132. The digital counter therefore counts to digital 3 and resets. Outputs of the digital counter 218 are applied to an interval generator 220 which comprises a logic circuit assembly for sequentially establishing a logical one level at each of its output lines 222, 224, 226 and 228.

Figure 12:
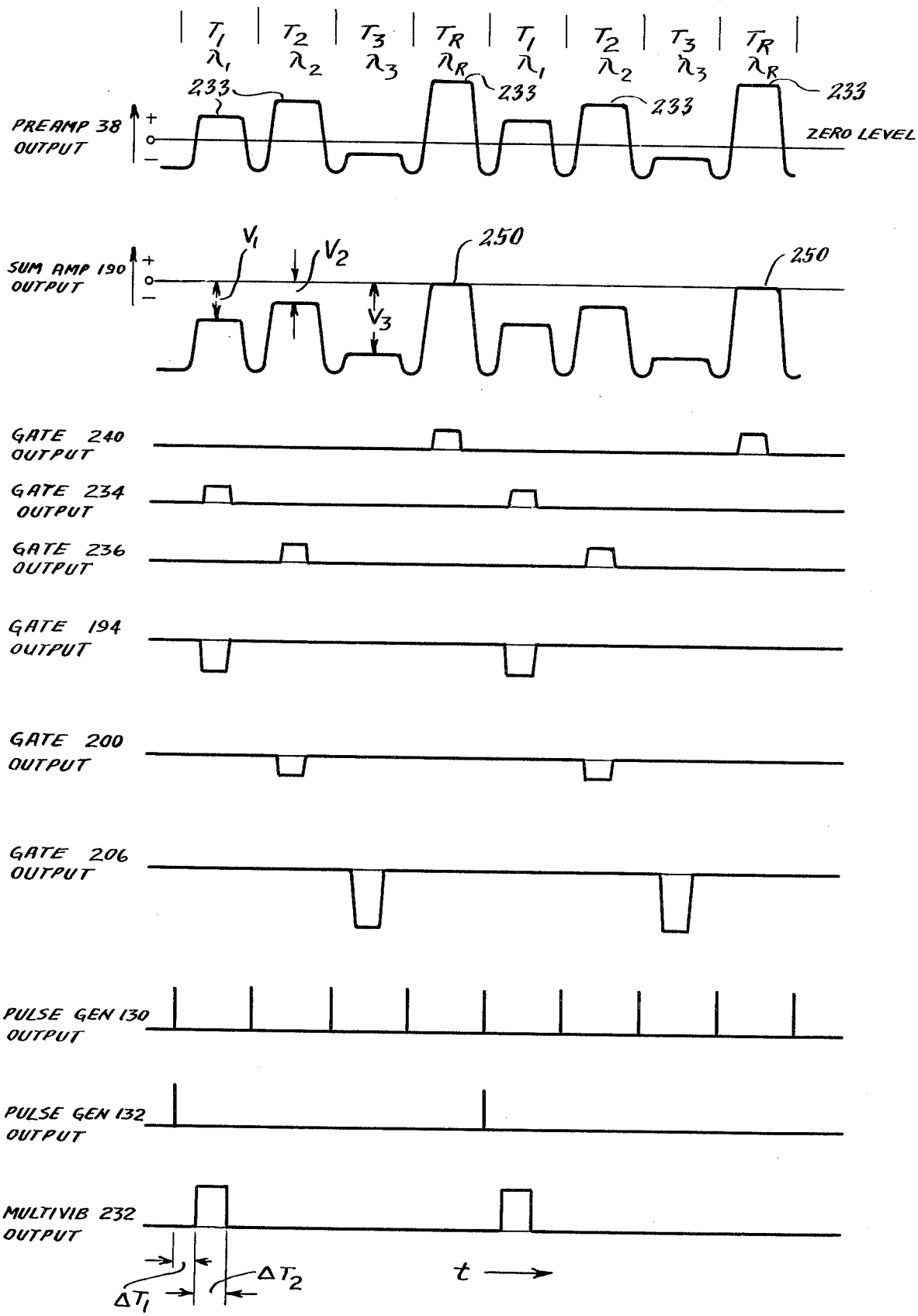
FIG. 12 is a diagram of the waveforms of electrical signals occurring at various locations in the circuit diagram of FIG. 11.

The pulse generator 130 also triggers a one-shot delay multivibrator 230. The output pulse from this multivibrator occurs for an interval of time $\Delta T_1$. A second one-shot multivibrator 232 is triggered by the trailing edge of this pulse and its triggering is therefore delayed in time by the interval $\Delta T_1$ (FIG. 12). As will be apparent from the discussion hereinafter, the delay $\Delta T_1$ of the pulse from the generator 230 is provided for causing the delayed pulse of generator 232 to coincide in time with relatively flat topped segments 233 (FIG. 12) of analog output signals from preamplifier 38. The period of the multivibrator $\Delta T_2$ is selected to be shorter than the interval of the relatively flat topped segments of these signals. The output of the one-shot multivibrator 232 is applied, along with the output of the interval generator 220, to AND gates 234-240 and provide gating command signals which sequentially enable the analog gates 194, 200, 206 and 212 respectively. The command signals thus generated are properly timed to assure sampling of the analog signals only during the relatively flat topped segments of the signal.

Referring to FIG. 12, it can be seen that the projection of a light beam having sequentially occurring components of differing wavelengths $\lambda_1$, $\lambda_2$, and $\lambda_3$ at intervals $T_1$, $T_2$ and $T_3$ respectively and having a reference wavelength $\lambda_r$ occurring at a reference interval $T_r$, results in a detached and amplified signal at the output of preamplifier 38 having the waveform illustrated. The relatively flat topped components illustrated in the waveform of the output of the preamplifier 36 represent the period of time during which the associated filter elements are positioned for transmitting radiant energy at the associated wavelength while the rising and trailing portions of the waveform occur when the traversing beam is approaching or departing from the associated filter element. The circuit arrangement of FIG. 11 is adapted to provide at terminals 242, 244 and 246 of channels 1, 2 and 3 respectively electrical signals which are proportional to variations in magnitude between the signal for a particular wavelength and the reference wavelength. The waveform of the preamplifier output signal indicates that this output signal varies in both the positive and negative direction around a zero voltage level with the relatively more negative variations corresponding to reduced or zero light level at the detector. The transient excursions between the sampling flat topped levels correspond, as indicated, to periods when the light beam is traversing from one filter member to an adjacent one. Readout of the differences in amplitude between a signal and the reference signal is provided by sampling the waveform at the center of the reference interval with an analog gate 212 and feeding back the signal via the integrator 192 to the summing amplifier 190. This negative feedback signal operates to clamp the flat top portion 250 of the reference signal at zero voltage level as indicated in FIG. 12 by the waveform representing the output signal of the summing amplifier 190. Here the flat top segments 250 of the reference signal components are shown clamped to zero potential. The clamped waveform is sampled during the flat top portion of the intervals $T_1$, $T_2$ and $T_3$ to provide the voltages $V_1$, $V_2$ and $V_3$ at the terminals 242, 244 and 246 respectively. Sampling is accomplished by the analog gate 194 of channel 1; the analog gate 200 of channel 2, and the analog gate 206 of channel 3. Each of the outputs of these gates is applied via associated low pass filters 196, 202 and 208 to associated high input impedance log amplifiers 198, 204 and 210 respectively. The filters 196, 202, and 208 remove the high frequency noise associated with the signal and provide a DC output which is maintained between successive intervals of time $T_1$, successive intervals of time $T_2$ or successive intervals of time $T_3$. The outputs at terminals 242 and 244 and 246 are converted to absorbance by the log amplifiers and are applied to the chart recorder 138 or digital display 140 of FIG. 1 to provide a simultaneous display of component response at the different wavelengths $\lambda_1$, $\lambda_2$ and $\lambda_3$.

The signals are also applied to the ratio circuit printer 142 which includes circuit means for forming the ratios between the signals of different channels and displaying this ratio. A suitable circuit means comprises a divider circuit and a suitable display means comprises a chart recorder, or a printing integrator.

Figure 13:
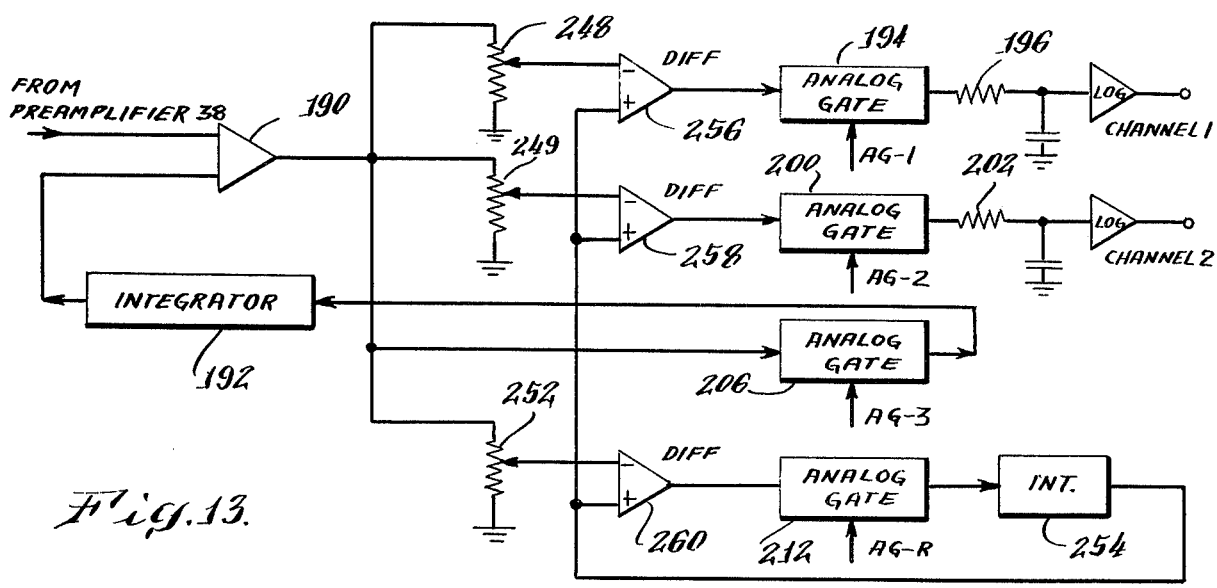
FIG. 13 is a circuit diagram, partly in block and partly in schematic form, illustrating an alternative arrangement of a portion of the circuit of FIG. 11 and having channel gain adjustment means; and, FIG. 14 is a diagram illustrating simultaneously recorded chromatograms produced with an analytical instrument constructed in accordance with features of this invention.

FIG. 13 illustrates an alternative arrangement of the circuit of FIG. 11 having individual channel gain adjustments for the signal processor which provide compensation for slightly varying optical filter energy transmission characteristics. For purposes of simplifying the drawings, only two channels are illustrated in FIG. 13. In this arrangement, the composite waveform at a time corresponding to zero light at the detector is sampled. Analog gate 206 samples the composite waveform at a time corresponding to zero light and its output is applied during this interval to the summing amplifier 190 via the integrator 192. Channel gain adjustment potentiometers 248 and 249 are provided. The voltage at potentiometer 248 during the interval $T_1$ corresponding to beam transit of filter element having a wavelength $\lambda_1$ is proportional to the light level at the detector. Potentiometer 248 is adjusted to introduce a desired multiplying constant which is used to compensate for a transmission error of the filter at the wavelength $\lambda_1$. The reference signal level, multiplied by a transmission factor N which is introduced by the adjustment of the potentiometer 252, is obtained at the output of an integrator 254. This output is coupled to difference amplifiers 256 and 258 in channels 1 and 2 and is subtracted from these gain adjusted signals. More particularly, during the interval $T_1$ (FIG. 12) the signal level occurring during this interval at the output of the integrator 254 is subtracted by the difference amplifier 256 and the resulting signal is sampled by the analog gate 194 to obtain the gain adjusted difference between the composite signal during the interval $T_1$ and the reference level signal. The circuit arrangement with respect to the low pass filtering, the use of log amplifiers and the generation of gating pulses is otherwise the same as was described with respect to FIG. 11.

Figure 14:
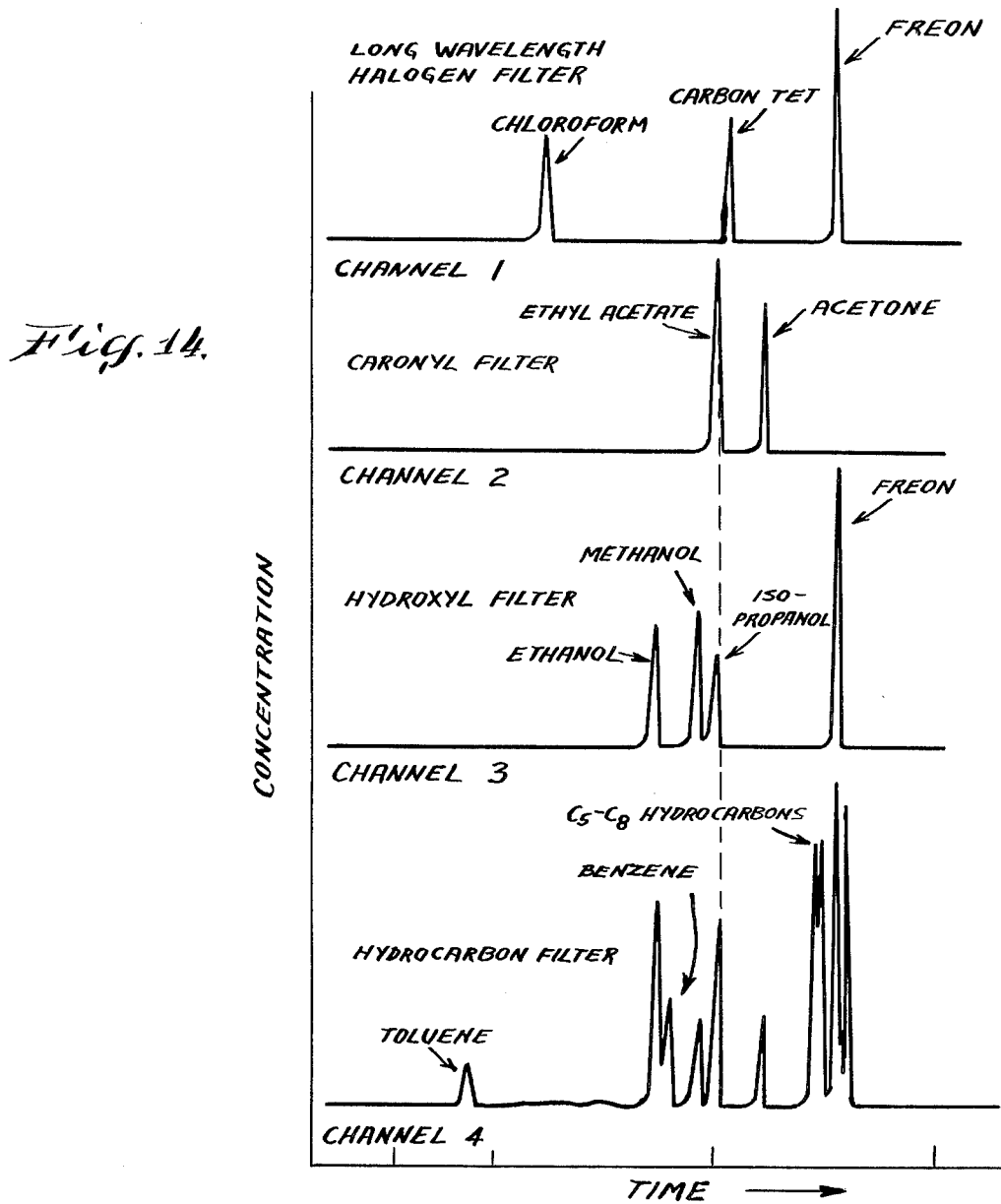

FIG. 14 illustrates a chart recording of an analysis employing a four channel analyzer of the type illustrated in FIG. 1. The chromatograms were obtained for a single sample injection. In this case the four channel filters provided are: channel 1 — halogen, channel 2 — carbonyl, channel 3 — hydroxyl and channel 4 hydrocarbon (paraffin and cycloparaffin, olefin and aromatic) functional groups. A 15- component mixture, in which each substance is present in about equal proportions, was used to demonstrate the capability of breaking down a mixture into different component categories. A 0.50 mm I.D., 50 ft. length S.C.O.T. column was prepared with carbowax 20M liquid phase. The column temperature was maintained at 80° C. A sample volume of 0.2 μl was provided with no inlet split. The filters used are indicated in FIG. 14. In addition to the convenient presentation aspect for chromatograms obtained with the multichannel detector, new qualitative information is also generated. The three alcohols have simultaneous response in both the CH and OH channels. The CH/OH ratio for each alcohol, however, varies significantly and increases with the chainlength. This chromatogram informs the analyst that isopropanol elutes first, which is the case with polar columns since isopropanol has the lowest polarity. With some columns the relative polarity-boiling point relationship affecting the order of component elution is not always predictable and varies with temperature. Thus, it is quite helpful to be able to obtain chainlength information to ascertain in which order components belonging to a given functionality elute.

Ethyl acetate and isopropanol are not separated in the hydrocarbon channel, which would be the case for other chromatography detectors, under these column and temperature conditions. However, examination of the channels 2 and 3 in this case informs the analyst that two components are actually present and also gives information on their functional groups. This means that more components can be spotted or separated with a given column which would not show up in a normal chromatogram. As a result, less efficient columns could be used for the analysis of complex mixtures or components which are difficult to separate on a given column.

An improved form of analytical instrument has been described which advantageously provides for simultaneous display of concentration at different wavelengths with a nondispersive type of multiwavelength photometer. The photometer is particularly advantageous in use as a selective detector for chromatography.

While particular embodiments of the invention have been described herein, it will be appreciated by those skilled in the art that variations may be made thereto without departing from the spirit of the invention and the scope of the appended claims.

What is claimed is:

1. A nondispersive chromatographic detector comprising:
   A. a radiant energy source;
   B. flow through sample cell means for positioning a sample for impingement by radiant energy from said source;
   C. chromatograph means including a separation means for causing a sample introduced to aid chromatograph to separate into components which elute successively in time from said separations means;
   D. means coupling said separation means to said flow through cell;
   E. first means for projecting radiant energy from said source toward said container means whereby a sample being analyzed is impinged by radiant energy and absorbs radiation and radiant energy transmitted by the sample is emitted from said container means;
   F. radiant energy intensity detection means;
   G. second means for projecting radiant energy emitted from said container toward said radiant energy detection means whereby said detection means provides an electrical indication representative of the intensity of radiant energy emitted from said container means;
   H. nondispersive radiant energy filter means for transmitting radiant energy incident thereon at a plurality of different predetermined analytical wavelengths, said filter means positioned in a path of projected radiant energy;
   I. means for causing radiant energy to periodically be projected at each of said plurality of analytical wavelengths; and,
   J. means coupled to said radiant energy detection means for providing a simultaneous indication of the intensity of radiant energy impinging on said detection means at each of said plurality of wavelengths.

2. The apparatus of claim 1 wherein said chromatograph means comprises a gas chromatograph.

3. The apparatus of claim 2 wherein said container means has a volume of less than about 20 microliters.

4. The apparatus of claim 1 wherein said chromatograph comprises a liquid chromatograph.

5. The apparatus of claim 1 wherein said filter means comprises a disk assembly having a plurality of filter members and is adapted for transmitting a predetermined analytical wavelength of radiant energy.

6. The apparatus of claim 5 wherein said means for causing radiant energy to periodically project through said filter means at each of said plurality of analytical wavelengths comprises means for rotating said filter means in the path of said radiant energy thereby causing different analytical filter members to be successively impinged by said radiant energy.

7. The apparatus of claim 5 wherein said means for causing radiant energy to periodically project through said filter means comprises means for supporting said filter means in a stationary position and means for deflecting the radiant energy for causing radiant energy to successively impinge upon different analytical filter members of said filter means.

8. The apparatus of claim 1 wherein said means for providing a simultaneous indication includes means for separating said electrical indications representative of a particular analytical wavelength into separate channels and for simultaneously displaying the signals of said channels.

9. The apparatus of claim 5 wherein said filter members are chosen to transmit at wavelengths or frequencies where absorptions occur which result from molecular functional groups thereby enabling identification of chemical structure of eluted components.

10. The apparatus of claim 9 wherein said filter members selectively sensitize detection means to chromatograph effluents.

11. The apparatus of claim 9 wherein each of said filter members is adapted to measure absorption at chemical functional group or frequencies.

12. The apparatus of claim 8 wherein said separating means comprises a time-shared, simultaneous, multi-wavelength detector having multiple output channels.

13. The apparatus of claim 8 wherein means are provided for forming and indicating a ratio between signal of different channels.

* * * * *